United States Patent
Richard et al.

(10) Patent No.: US 7,427,272 B2
(45) Date of Patent: Sep. 23, 2008

(54) METHOD FOR LOCATING THE MECHANICAL AXIS OF A FEMUR

(75) Inventors: Alain Richard, Montreal (CA); Herbert André Jansen, Montreal (CA); Eric Brosseau, Montreal (CA)

(73) Assignee: Orthosoft Inc., Montréal (CA)

( * ) Notice: Subject to any disclaimer, the term of this patent is extended or adjusted under 35 U.S.C. 154(b) by 504 days.

(21) Appl. No.: 10/618,846

(22) Filed: Jul. 15, 2003

(65) Prior Publication Data

US 2005/0015022 A1 Jan. 20, 2005

(51) Int. Cl.
*A61B 5/103* (2006.01)
(52) U.S. Cl. .................. 600/587; 600/595; 606/89; 606/130
(58) Field of Classification Search .............. 606/89, 606/130; 600/595, 587
See application file for complete search history.

(56) References Cited

U.S. PATENT DOCUMENTS 5,611,353 A * 3/1997 Dance et al. ............... 600/595

2003/0069591 A1 4/2003 Carson et al.

FOREIGN PATENT DOCUMENTS

| WO | WO 00/48507 | 8/2000 |
| WO | WO 02/17798 | 3/2002 |
| WO | WO 02/47559 | 6/2002 |
| WO | WO/0247559 | * 6/2002 |

* cited by examiner

*Primary Examiner*—Brian L. Casler
*Assistant Examiner*—John F Ramirez
(74) *Attorney, Agent, or Firm*—Ogilvy Renault LLP

(57) ABSTRACT

There is described a method for determining a mechanical axis of a femur using a computer aided surgery system having an output device for displaying said mechanical axis, the method comprising: providing a position sensing system having a tracking device capable of registering instantaneous position readings and attaching the tracking device to the femur; locating a center of a femoral head of the femur by moving a proximal end of the femur to a first static position, acquiring a fixed reading of the first static position, repeating the moving and the acquiring for a plurality of static positions; and locating the centre by determining a central point of a pattern formed by the plurality of static positions; digitizing an entrance point of the mechanical axis at a substantially central position of the proximal end of the femur; and joining a line between the entrance point and the center of rotation to form the mechanical axis.

21 Claims, 6 Drawing Sheets

```
┌─────────────────────────────────────────────┐
│ PROVIDING A POSITION SENSING SYSTEM HAVING A│  16
│  TRACKING DEVICE CAPABLE OF REGISTERING     │
│   INSTANTANEOUS POSITION READINGS AND       │
│  ATTACHING THE TRACKING DEVICE TO THE FEMUR │
└─────────────────────────────────────────────┘
                       │
                       ▼
┌─────────────────────────────────────────────┐  17
│  LOCATING A CENTER OF THE FEMORAL HEAD BY   │
│   MOVING A PROXIMAL END OF THE FEMUR TO A   │
│     FIRST STATIC POSITION ACQUIRING A FIXED │
│       READING OF THE FIRST STATIC POSITION  │
│   REPEATING THE MOVING AND THE ACQUIRING FOR│
│     A PLURALITY OF STATIC POSITIONS AND     │
│     LOCATING THE CENTER BY DETERMINING A    │
│   CENTRAL POINT OF A PATTERN FORMED BY THE  │
│         PLURALITY OF STATIC POSITIONS       │
└─────────────────────────────────────────────┘
                       │
                       ▼
          ┌──────────────────────────┐  18
          │ DIGITIZING AN ENTRANCE POINT │
          │   OF THE MECHANICAL AXIS │
          └──────────────────────────┘
                       │
                       ▼
          ┌──────────────────────────┐  19
          │ JOINING THE ENTRANCE POINT AND │
          │  THE CENTER OF THE FEMORAL│
          │   HEAD TO FORM THE AXIS  │
          └──────────────────────────┘
```

FIG. 1

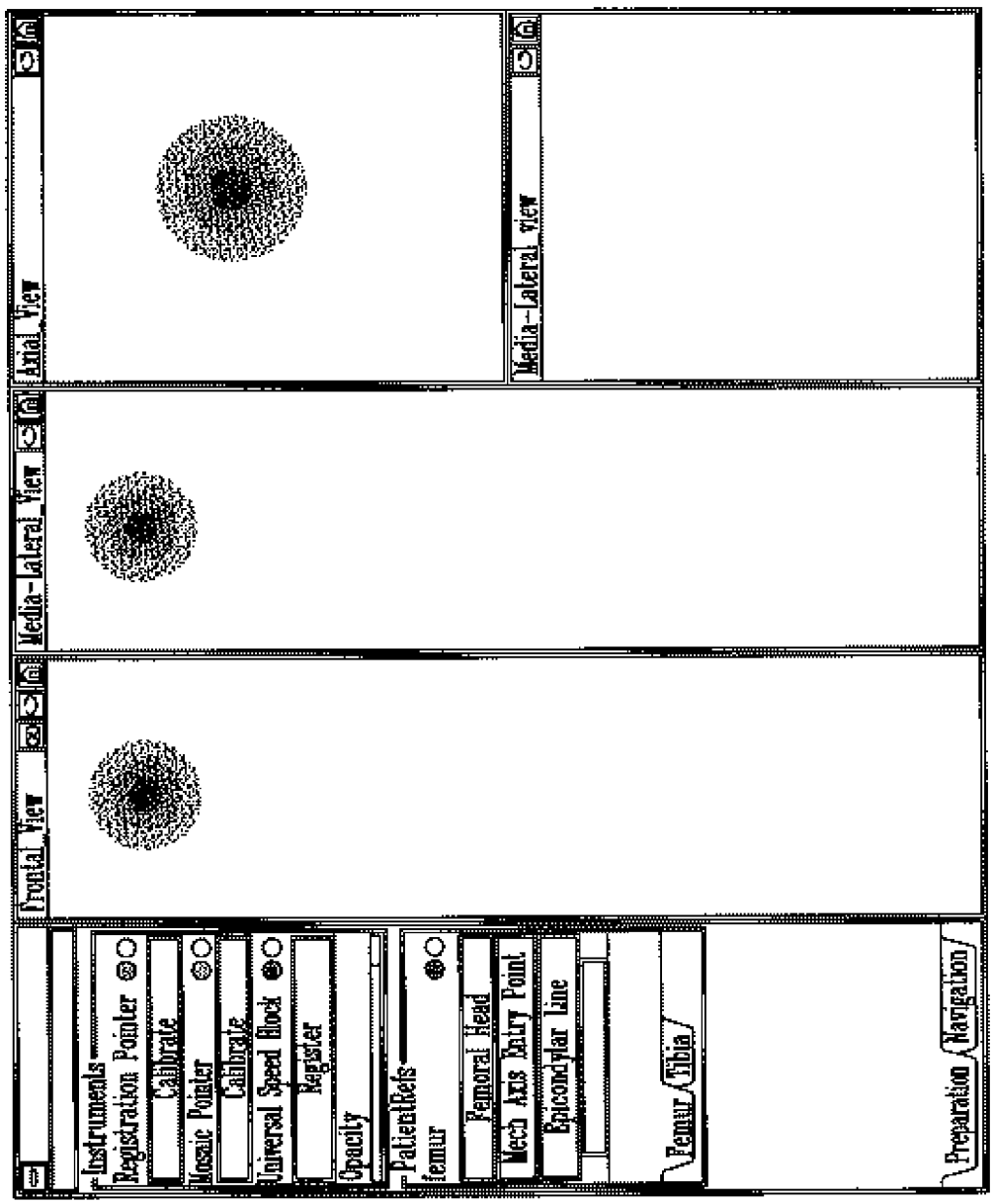

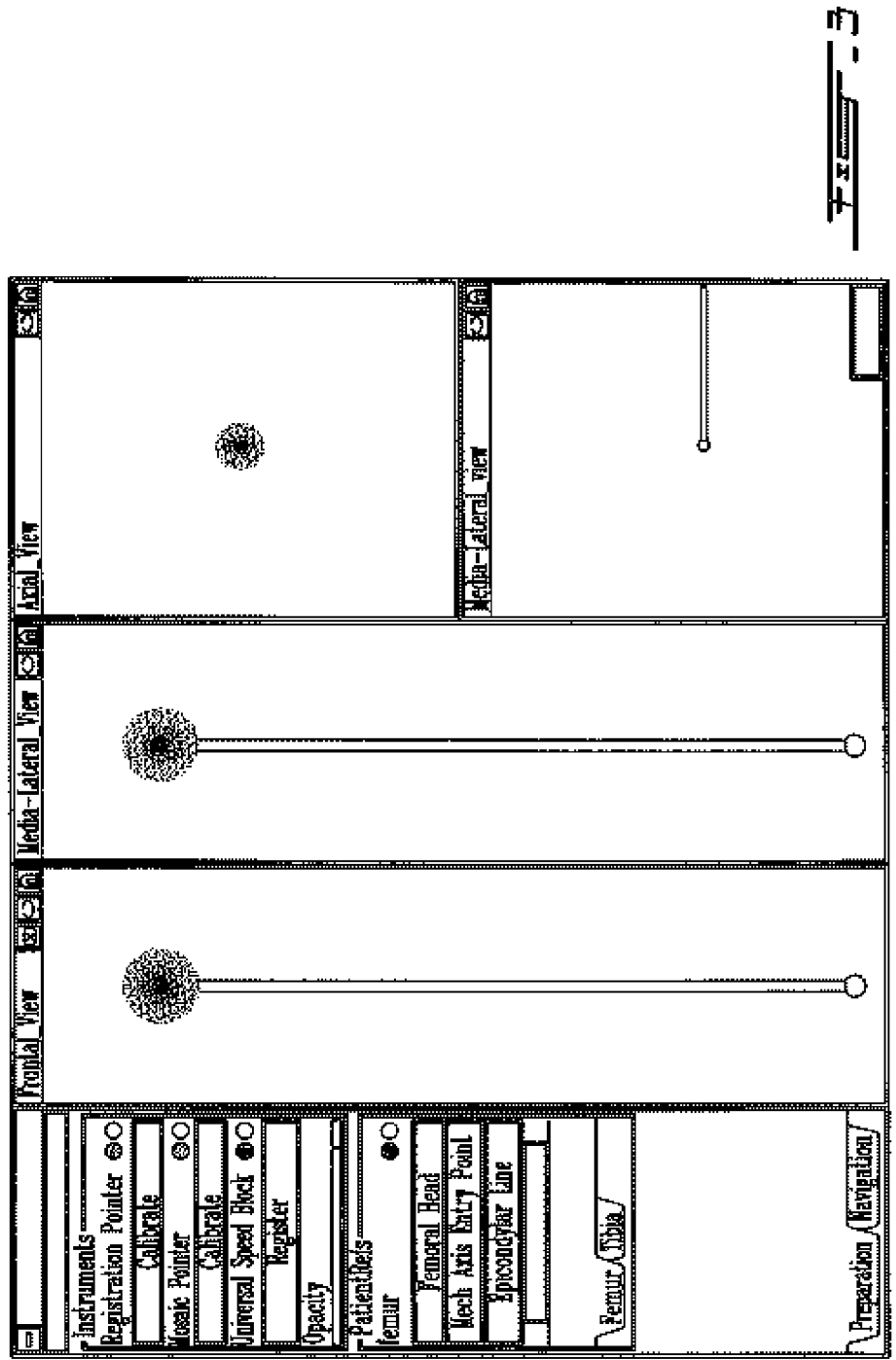

METHOD FOR LOCATING THE MECHANICAL AXIS OF A FEMUR

FIELD OF THE INVENTION

The invention relates to the field of computer-assisted surgery. More specifically, it relates to determining the mechanical axis of a femur and the center of a femoral head of femur during computer assisted surgery.

BACKGROUND OF THE INVENTION

While Computer-Tomographic(CT)-based Computer Assisted Surgery (CAS) systems are widely known in the art, CT-less CAS systems are slowly emerging as the technology of choice for North America and Europe. It is desirable to cut down the pre-operative time a surgeon must spend to prepare a surgery. It is also desirable to provide applications that can use other media than CT-scans, when these are not available. The CT-less system reduces pre-operative time and instrument calibration time, especially in simple surgeries, and in the case of more complex surgeries, the CT-less system can be combined with CT-based applications.

A CT-less intra-operative bone reconstruction system advantageously provides a surgeon with visual confirmation of the tasks he is performing during the surgery. In pending U.S. patent application Ser. No. 10/345,403 to the present applicant, there is described a method and system for intra-operatively presenting an approximate model of an anatomical structure by collecting a cloud of small surfaces. The cloud of small surfaces is gathered with a registration pointer having an adapted tip capable of making contact with the surface of an anatomical structure and registering the normal at the point of contact. Reconstructing and registering anatomical structures intra-operatively is at the core of CT-less CAS systems.

When performing surgery to the lower limbs, it is important to determine the mechanical axis of the leg. The mechanical axis refers to the axis formed by a line drawn from the center of the femoral head to the center of the knee joint and a line drawn from the center of the knee joint to the center of the ankle joint. In perfectly aligned leg, the mechanical axis forms a straight line.

Determining the mechanical axis of a leg comprises locating the center of the femoral head. It is known in the art of computer-assisted surgery to locate the center of the femoral head by dynamically registering the relative position of the femur while rotating the proximal end in a circular pattern. However, this technique is vulnerable to noise, thereby affecting the quality of the readings by the position sensing system. The level of accuracy obtained also varies depending on how long the rotation is maintained for and with how much precision the system can register the points while the bone is in motion. Furthermore, the motion of the femur for the registration process may cause the hipbone to move and this can introduce further errors into the measurements.

Detecting the femoral head is a crucial process that will influence the end result of the surgery. There is therefore a need to develop a system and method of femoral head detection that overcomes the drawbacks of the state of the art and guarantees a certain level of accuracy.

SUMMARY OF THE INVENTION

Accordingly, an object of the present invention is to overcome the influence of noise for tracking devices and improve accuracy when locating the center of the femoral head of a femur.

According to a first broad aspect of the present invention, there is provided a method for determining a mechanical axis of a femur using a computer aided surgery system having an output device for displaying said mechanical axis, the method comprising: providing a position sensing system having a tracking device capable of registering instantaneous position readings and attaching the tracking device to the femur; locating a center of a femoral head of the femur by moving a proximal end of the femur to a first static position, acquiring a fixed reading of the first static position, repeating the moving and the acquiring for a plurality of static positions; and locating the centre by determining a central point of a pattern formed by the plurality of static positions; digitizing an entrance point of the mechanical axis at a substantially central position of the proximal end of the femur; and joining a line between the entrance point and the center of rotation to form the mechanical axis.

Preferably, the system automatically registers instantaneous positions periodically and averages a plurality of the instantaneous positions to determine a static position.

BRIEF DESCRIPTION OF THE DRAWINGS

These and other features, aspects and advantages of the present invention will become better understood with regard to the following description and accompanying drawings wherein:

FIG. 1 is a flowchart of the preferred embodiment of the invention;

FIG. 2 shows the center of the femoral head on the user interface;

FIG. 3 shows the mechanical axis on the user interface;

DETAILED DESCRIPTION OF THE PREFERRED EMBODIMENT

Figure 4:
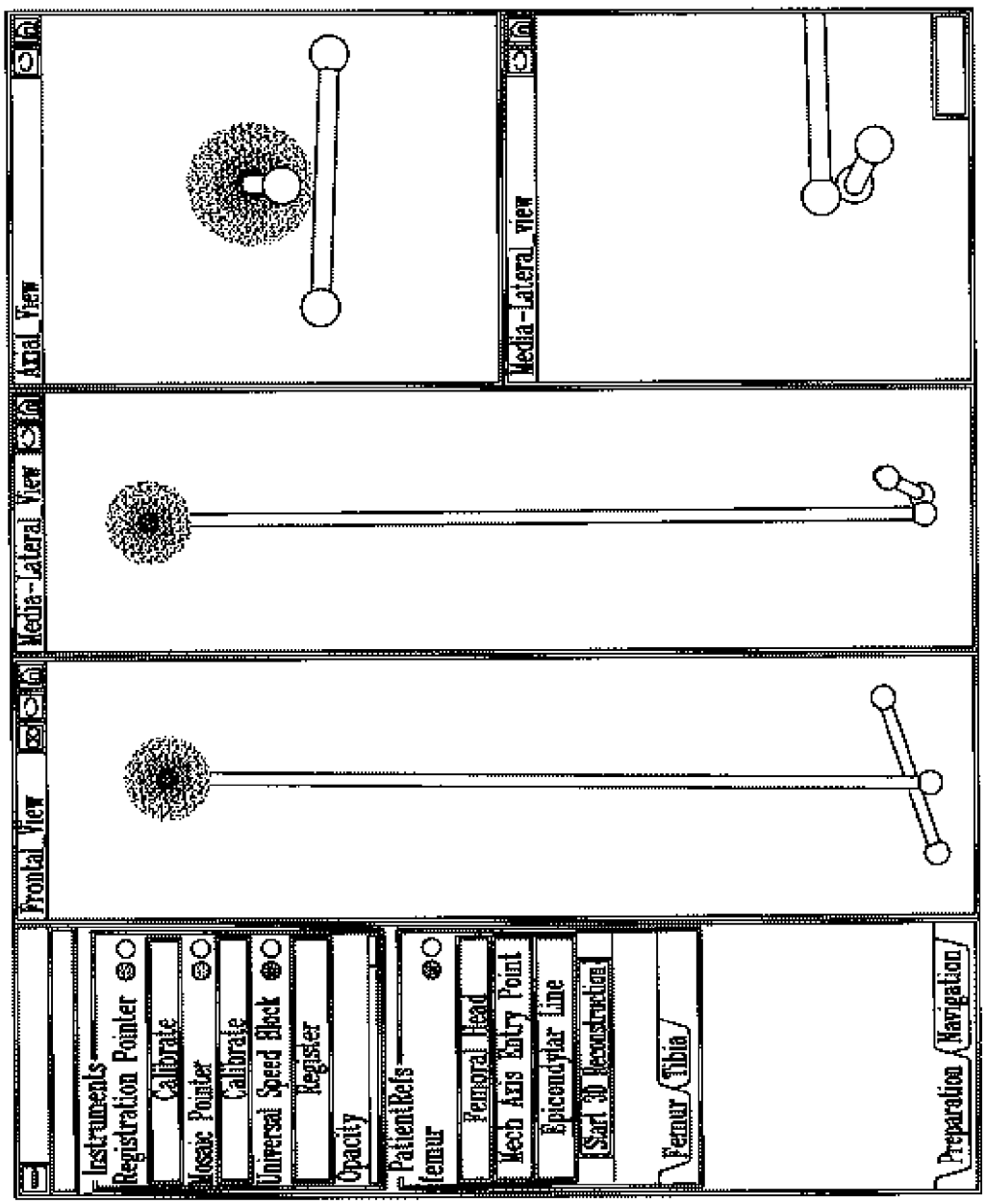
FIG. 4 shows the mechanical axis and the epicondylar axis on the user interface.

In a preferred embodiment of the invention, a Polaris™ optical camera is used with a Navitrack™ system sold by Orthosoft, Inc. A femoral tracker is optimally placed at an anterior position with respect to the sagittal anatomical axis and a lateral position with respect to the frontal anatomical axis. Ideally, the anterior position should be about 45 degrees and the lateral position should be about 10 degrees. The position to optimize accuracy for the bone trackers is about 12 cm from the knee joint facing the camera.

FIG. 1 is a flowchart describing the steps used to determine the mechanical axis of the femur bone during surgery. The first step is to provide a position sensing system having a tracking device capable of registering instantaneous position readings and attaching the tracking device to the femur 16. The next step is to locate the center of the femoral head 17. This point will be used in calculating the mechanical axis. To locate the center of the femoral head, the proximal end of the femur is placed in a first static position. A fixed reading of the first static position of the femur is acquired by the position sensing system. This action is repeated for a plurality of static positions. The center of the femoral head is then located by determining a central point of the pattern that is formed by the plurality of static positions. Also needed to calculate the mechanical axis is locating the entrance point of the mechanical axis 18. This point is in the notch found at the femoral distal end of the femur bone, and matches the intra-medullar rod entrance point, which surgeons are familiar with. The surgeon attempts to locate this point by physically palpating the area and once the center is located, this point is digitized by the digitizing tool and recorded in the memory of the system. Once the two end points have been identified, a line is formed to join them together and create the mechanical axis 19. The axis is then displayed on an output device to visually assist the surgeon throughout the surgery.

The detection of the femoral head is ideally performed by taking fourteen static points of the femur with respect to a fixed pelvis. That is to say, the pelvis must remain fixed throughout the acquisition of each point until the end. Each acquisition of a static point should be done by immobilizing the tracked leg on the operating table and waiting for an indication that the system has registered the position. This indication may be visual on the output device, or an audio signal such as a beep emitted by the system. Alternatively, the surgeon can take anywhere between 7 and 20 positions. The surgeon can choose to use a pelvic reference or not, and by doing so, increases the algorithm accuracy by recording the small oscillation movements of the pelvis during the acquisition.

The surgeon should take points that would best fit a conical pattern with the femoral tracker. The pelvis and the optical camera should stand immobile during the whole process to reach a good level of accuracy. Between each data acquisition, the femoral tracker should move a minimum of 20 mm to get better results. A judicious positioning of the leg at each step is important.

The position sensing system may be of the type that automatically registers instantaneous positions periodically. In that case, the surgeon stays in a static position for a minimum amount of time while the system registers a plurality of readings. The position is then determined by taking an average of all of the instantaneous positions that are within a certain range. When the range changes by a large amount, the system detects the change in position and does not include the readings in the average.

Alternatively, the system reacts to user input to register a position reading. In that case, the surgeon places the bone in a static position and enables the system to register the position. This can be done a variety of ways, such as clicking a button on a mouse or keyboard.

The large sphere in FIG. 2 represents the center of the femoral head. Several views are provided by the display, such as frontal, medio-lateral, and axial. The pattern of the rotation is registered and the center of rotation is identified as the center of the femoral head. After a registration tool is used to digitize the entrance point of the mechanical axis in the femur bone, a stretchable line that originates at the center of the sphere and moves with the registration tool represents the mechanical axis. This feature allows the user to correct the location of the femoral mechanical axis by clicking on the mechanical entrance point and changing its position. This axis is used as the main axis of the reference system. FIG. 3 shows the user interface displaying the center of the femoral head, the mechanical axis entrance point, and the thin cylinder that represents the axis. The entry point of the mechanical axis should be defined as the entry point of the intra-medullary rod. The mechanical axis will then be used as the main axis of a coordinate system, which will be used to provide numerical values during navigation. The user can re-enter the entry point of the mechanical axis, as many times as desired, and the system will update the axis.

Figure 6:
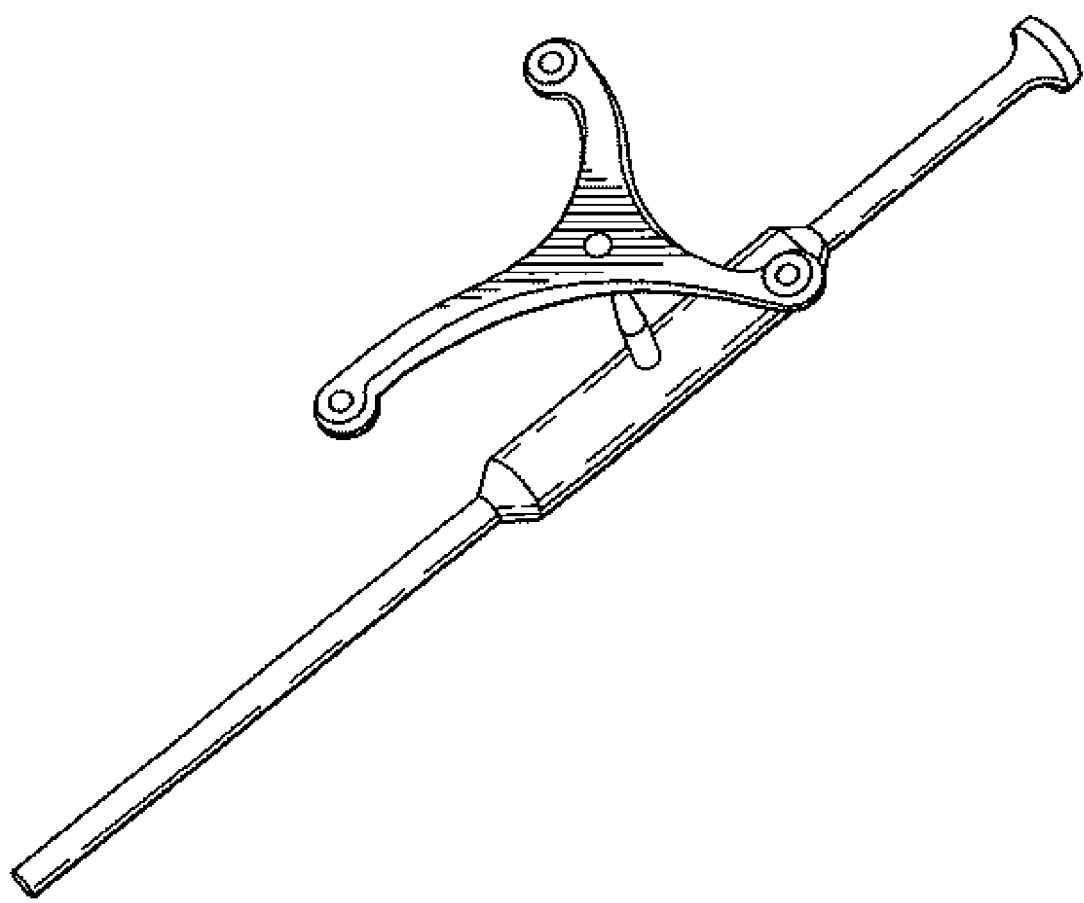
FIG. 6 is a diagram of a digitizing tool with an adaptive tip.

The next operation is the digitizing of the epicondyles, as can be seen in FIG. 4. Two points are used to describe a 3D axis by digitizing the epicondyles using the registration tool. The line formed between the epicondyles represents the epicondylar axis. The user can easily modify the two endpoints at any moment. The epicondylar axis is used as the second axis of the reference system and is required to provide axial numerical information during navigation. To facilitate the identification of the epicondyles, a MOSAIC™ pointer could be used to reconstruct them. This pointer is illustrated in FIG. 6 and will be described in more detail below. After having reconstructed the epicondyles, the user can re-digitize the landmarks more accurately.

Figure 5:
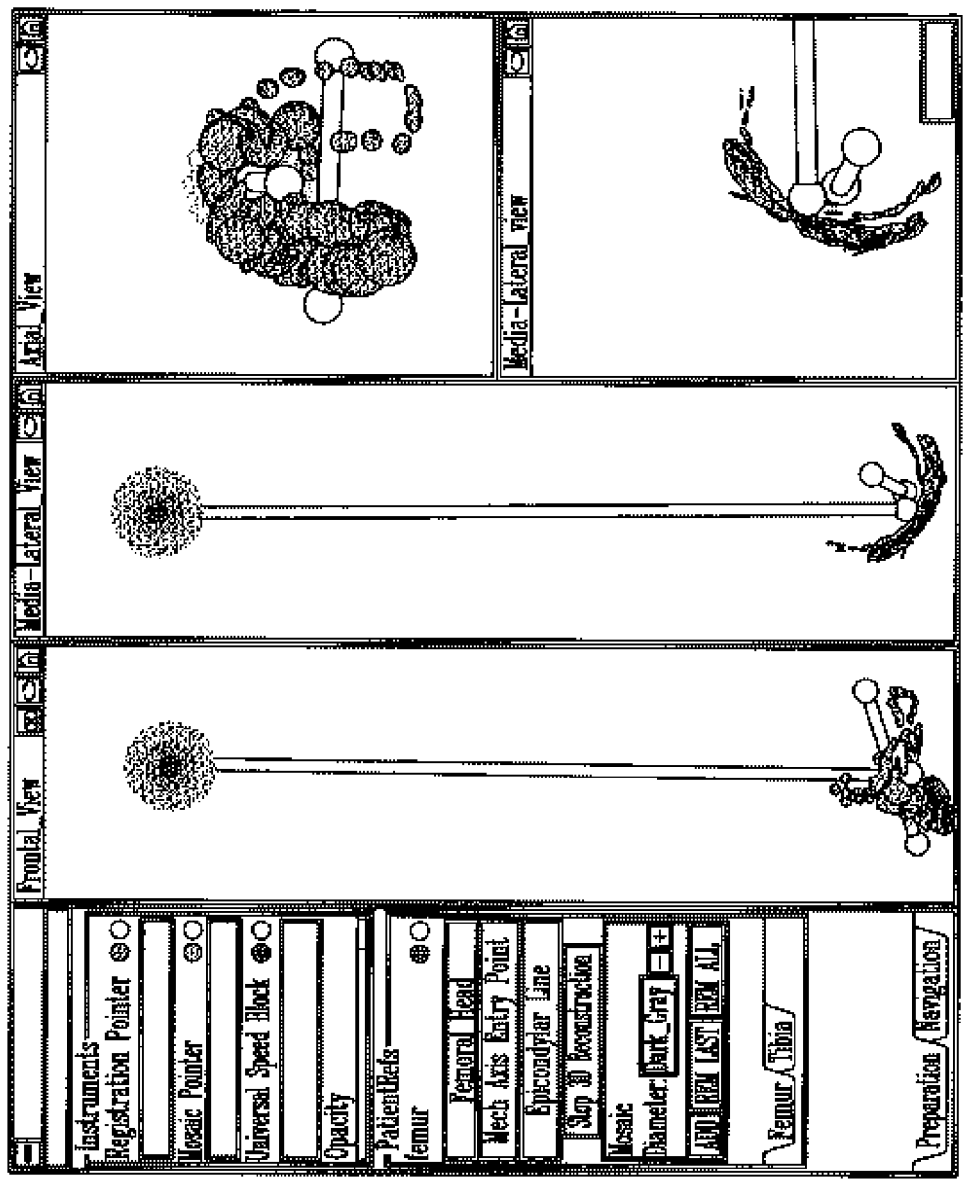
FIG. 5 shows the mosaic reconstruction of a bone.

Surface model reconstruction is a process that allows the user to digitize small surfaces instead of points only. These surfaces can be small circles, as can be seen from FIG. 5. The small circle is physically present on the tip of the registration tool as a small, flat disc. The size of the disc (radius) is chosen as a compromise between accuracy and time. It is counterproductive to ask a surgeon to take hundreds of points when digitizing the surface of a bone. However, the more points taken, the better the representation of the bone and the more accurate the model. The size can also vary depending on the morphology of the bone surface, affecting the precision of the tool. For example, the disc could cover an area of 1 cm$^2$. The disc must be flat on the surface to register as much surface as possible. The tool also registers the normal at the point of contact between the flat disc surface and the bone. As each digitized surface is registered, it appears on the output display. A sufficient amount of digitized surfaces will represent an approximate model of the entire surface. The model is formed as a mosaic of circular surfaces. This reconstruction is done in real time.

From the input data gathered, the approximate model reconstruction can be morphed into an actual three-dimensional model. Once this reconstruction is done, tools used for the surgery can be tracked with respect to this model, thereby allowing the surgeon to navigate with tools and have a reference in the body.

FIG. 6 is the preferred embodiment of the digitizing tool, the pointer, to be used in the digitizing process. The tool is equipped with a position-sensing device, such as those known in the field of tracking, having three position identifying devices. In this embodiment, both ends of the tool can serve as a digitizing tip, each end having a different radius. The smaller end can be used on anatomical surfaces that do not easily accommodate the flat surface of the tool. The larger end can be used on flatter anatomical surfaces. The user selects on the computer which end is used. Alternatively, there can be automatic detection of the end being used, such as the computer recognizing the radius of the disc surface when it is placed on the bone surface. For the actual registration of the small surfaces, this can be achieved in several ways. For example, there can be a button on the tool that controls the digitizing. Alternatively, this can be done by pressing a key on a keyboard to select a point to be digitized. Also alternatively, digitizing can be triggered by a rotating action of the tool by a quarter turn. It can be appreciated that alternative embodiments for the registration tool are possible. For example, other multi-purpose combinations can be made. One end can be an awl, a screwdriver, or a probe, while the other end is a digitizer. Similarly, the tool can be a single-ended digitizer as well.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method for determining a mechanical axis of a femur using a computer aided surgery system having an output device for displaying said mechanical axis, the method comprising:
   providing a position sensing system having a tracking device capable of registering instantaneous position readings and attaching said tracking device to said femur;
   locating a center of rotation of a femoral head of said femur by moving a proximal end of said femur to a first static position, acquiring a fixed reading of said first static position, repeating said moving and said acquiring for a plurality of static positions; and locating said centre by determining a central point of a pattern formed by said plurality of static positions;
   digitizing an entrance point of said mechanical axis at a substantially central position of said proximal end of said femur;
   joining a line between said entrance point and said center of rotation to form said mechanical axis; and
   displaying said mechanical axis on an output device without reference to an image of said femur acquired pre-operatively or intra-operatively using a medical imaging device.

2. A method as claimed in claim 1, wherein said position sensing system automatically registers said instantaneous position readings periodically and said acquiring a fixed reading comprises taking an average value of a plurality of said instantaneous position readings to determine said static position.

3. A method as claimed in claim 1, wherein said position sensing system responds to user input to register said instantaneous position readings and said acquiring a fixed reading comprises enabling said position sensing system to register a single instantaneous position reading.

4. A method as claimed in claim 1, wherein said pattern formed by said plurality of static positions is a conical pattern.

5. A method as claimed in claim 1, wherein said acquiring a fixed reading comprises determining a position of said proximal end relative to a reference.

6. A method as claimed in claim 5, wherein said reference is a fixed reference placed on a pelvis bone adjacent to said femur.

7. A method as claimed in claim 1, wherein said repeating said moving comprises waiting for a signal from an acquisition system that said fixed reading has been acquired before moving to a next static position.

8. A method as claimed in claim 7, wherein said signal is an audio sound.

9. A method as claimed in claim 1, wherein said repeating said moving comprises moving said proximal end at least 20 mm to a next static position.

10. A method as claimed in claim 1, wherein said digitizing comprises applying an instrument to a surface of said bone such that a point and a normal axis to said point are determined.

11. A method as claimed in claim 1, wherein said substantially central position is determined visually.

12. A method as claimed in claim 1, wherein said bone is a femur, said first end is a femoral head of said femur, and said substantially central position is determined by locating an inter-condylar notch.

13. A method as claimed in claim 12, wherein said inter-condylar notch is located by digitizing a medial and a lateral epicondyle at said second end of said femur, forming an epicondylar axis, and determining a center of said epicondylar axis.

14. A system for determining a mechanical axis of a femur, the system comprising:
   a position sensing system having a tracking device adapted to register instantaneous position readings of said femur;
   an acquisition module adapted to acquire data from said position sensing system and store fixed readings of a plurality of static positions of a proximal end of said femur and a digitized reading of an entrance point of said mechanical axis;
   a computing module adapted to locate a center of a femoral head of said femur by determining a central point of a pattern formed by said plurality of static positions and joining a line between said entrance point and said center of a femoral head, thereby representing said mechanical axis; and
   an output device adapted to display said mechanical axis, wherein said mechanical axis is determined and displayed on said output device without reference to an image of said femur acquired pre-operatively or intra-operatively using a medical imaging device.

15. A system as claimed in claim 14, wherein said position sensing system automatically registers said instantaneous position readings periodically, and said acquisition module is adapted to take an average value of a plurality of said instantaneous position readings to determine said static positions.

16. A system as claimed in claim 14, wherein said position sensing system responds to user input to register said instantaneous position readings.

17. A system as claimed in claim 14, wherein said acquisition module determines a position of said proximal end relative to a reference.

18. A system as claimed in claim 17, wherein said reference is a fixed reference placed on a pelvis bone adjacent to said femur.

19. A system as claimed in claim 14, wherein said acquisition module provides a signal that said fixed readings have been acquired in between each acquisition.

20. A system as claimed in claim 19, wherein said signal is an audio sound.

21. A system as claimed in claim 14, wherein said digitized reading of an entrance point is a point and a normal axis to said point.

* * * * *